US006497667B1

(12) United States Patent
Miller et al.

(10) Patent No.: US 6,497,667 B1
(45) Date of Patent: Dec. 24, 2002

(54) ULTRASONIC PROBE USING RIBBON CABLE ATTACHMENT SYSTEM

(75) Inventors: David G. Miller, North Andover, MA (US); Rodney J. Solomon, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 2 days.

(21) Appl. No.: 09/919,465

(22) Filed: Jul. 31, 2001

(51) Int. Cl.[7] .................................................. A61B 8/14

(52) U.S. Cl. ....................... 600/459; 600/462; 600/463; 29/23.35; 128/916

(58) Field of Search ................................. 600/459–472; 310/334–336; 29/25.35; 73/618; 128/916

(56) References Cited

U.S. PATENT DOCUMENTS 5,085,221 A * 2/1992 Ingebrigtsen et al. ....... 600/446
5,267,221 A 11/1993 Miller et al. ................ 367/140
5,857,974 A * 1/1999 Eberle ........................ 600/462

OTHER PUBLICATIONS

U.S. Utility Patent Application entitled "System for Attaching an Acoustic Element to an Integrated Circuit" inventors: David G. Miller and Bernard Savord, pp. 1–29, 9 Sheets of Formal Drawings.

* cited by examiner

*Primary Examiner*—Marvin M. Lateef
*Assistant Examiner*—Ruby Jain
(74) *Attorney, Agent, or Firm*—John Vodopia

(57) ABSTRACT

An ultrasonic transducer probe uses one or more ribbon cables to attach the transducer elements to the probe wiring. Electrical conductors within a first ribbon cable attach to corresponding lands on an end of an integrated circuit and, electrical conductors within additional ribbon cables attach to corresponding lands on circuit boards. The circuit boards distribute the electrical signals from the attached ribbon cables to additional lands on another end of the integrated circuit.

23 Claims, 6 Drawing Sheets

ULTRASONIC PROBE USING RIBBON CABLE ATTACHMENT SYSTEM

TECHNICAL FIELD

The present invention relates generally to ultrasonic transducers and, more particularly, to an ultrasonic probe using ribbon cable to attach the electrical wiring to the transducer elements.

BACKGROUND OF THE INVENTION

Ultrasonic transducers have been available for quite some time and are particularly useful for non-invasive medical diagnostic imaging. Ultrasonic transducers are typically formed either of piezoelectric elements or of micro-machined ultrasonic transducer (MUT) elements. The piezoelectric elements typically are made of a piezoelectric ceramic such as lead-zirconate-titanate (PZT), with a plurality of elements being arranged to form a transducer. A MUT is formed using known semiconductor manufacturing techniques resulting in a capacitive ultrasonic transducer cell that comprises, in essence, a flexible membrane supported around its edges over a silicon substrate. By applying contact material, in the form of electrodes, to the membrane or to a portion of the membrane, and to the base of the cavity in the silicon substrate, and then applying appropriate voltage signals to the electrodes, the MUT may be energized such that an appropriate ultrasonic wave is produced. Similarly, when electrically biased, the membrane of the MUT may be used to receive ultrasonic signals by capturing reflected ultrasonic energy and transforming that energy into movement of the electrically biased membrane, which then generates a receive signal.

The ultrasonic transducer elements may be arranged in a one or multi-dimensional array and combined with control circuitry forming a transducer assembly, which is then further assembled into a housing possibly including additional control electronics, in the form of electronic circuit boards, the combination of which forms an ultrasonic probe. A large number of ultrasonic elements typically comprise an array, thereby requiring a large number of electrical connections as each element should be connected to a separate electrical lead and to a ground plane.

There are different ultrasonic probes available depending on the type and the location of the tissue, organ, or other structure in the body being imaged. One of the more specialized ultrasonic probes is the transesophageal probe (TEE probe), which is formed on a long slender body. This configuration places severe limitations on the mechanical and electrical design of the probe and presents significant wiring challenges. Specifically, the TEE probe has considerable space restraints that must be observed when designing the probe. This affects both the size of the array and the volume of space available to connect each element in the array to a suitable wiring system. While known one-dimensional arrays typically have a fine horizontal pitch (pitch is the center to center distance between the elements in the array) and a coarse vertical pitch, many proposed two-dimensional arrays are finely pitched in both dimensions having horizontal and vertical pitch dimensions on the order of 100–160 $\mu$m (microns).

The TEE probe is an invasive probe, and, as such, space inside the probe body for making electrical connections is severely limited. In the past, it has been difficult to design a TEE probe having a significant number of electrical leads within the space allowed by the probe design, and it has been difficult to connect a large number of transducer array elements to their respective individual conductors.

Therefore, it would be desirable to be able to be able to connect a large number of transducer elements to their respective conductors in the limited space available in an ultrasonic transducer probe.

SUMMARY

An ultrasonic transducer probe uses one or more ribbon cables to attach the transducer elements to the probe wiring. Electrical conductors within a first ribbon cable attach to corresponding lands on an end of an integrated circuit and, electrical conductors within additional ribbon cables attach to corresponding lands on circuit boards. The circuit boards distribute the electrical signals from the attached ribbon cables to additional lands on another end of the integrated circuit.

Other systems, methods, features, and advantages of the invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The present invention, as defined in the claims, can be better understood with reference to the following drawings. The components within the drawings are not necessarily to scale relative to each other, emphasis instead being placed upon clearly illustrating the principles of the present invention.

DETAILED DESCRIPTION OF THE INVENTION

The invention to be described hereafter is applicable to any wiring installation where it is desirable to connect a large number of conductors to an integrated circuit, and is particularly useful when the conductors are compatible with a ribbon-type cable.

Figure 1:
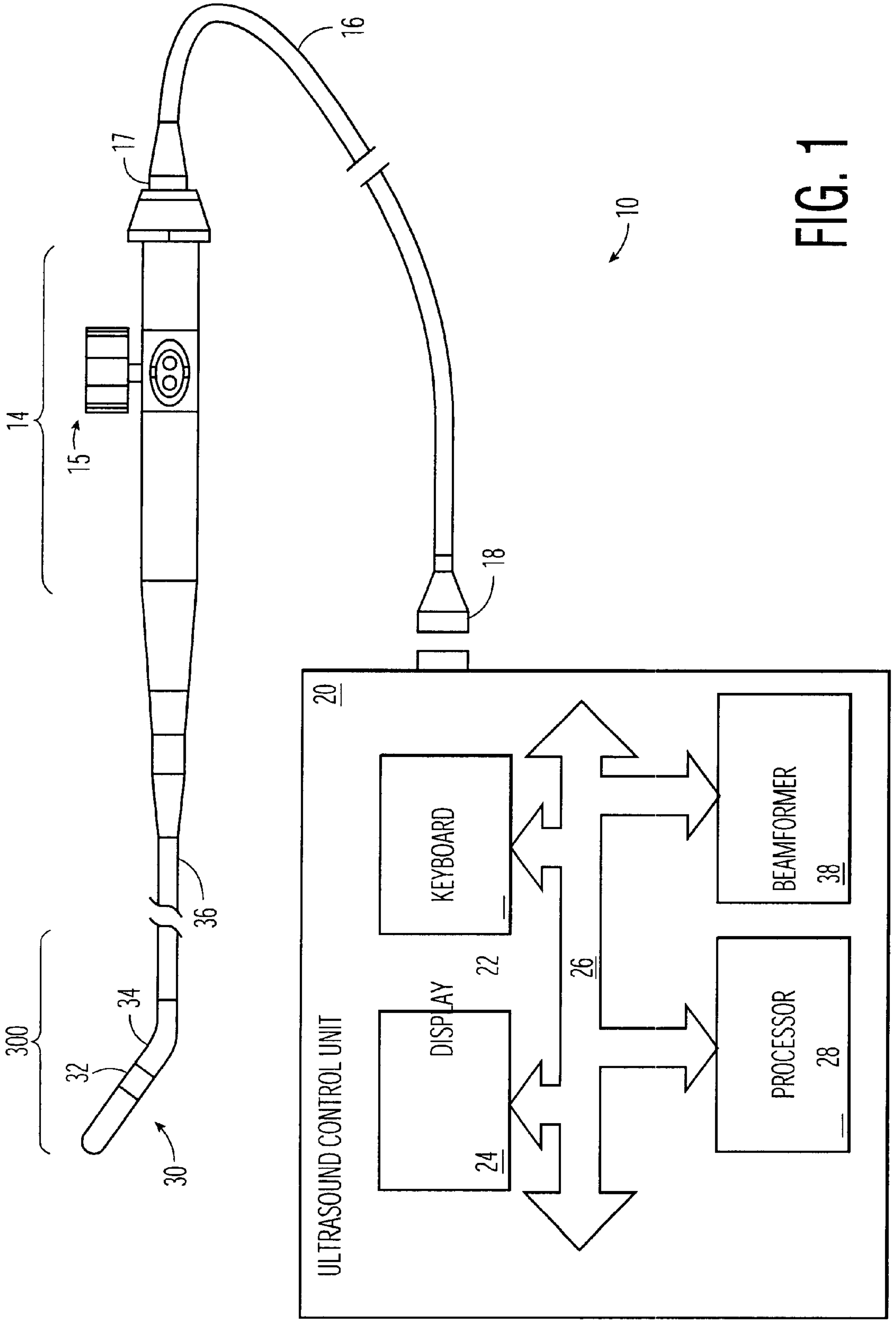
FIG. 1 is an illustration of an ultrasound system including a transesophageal (TEE) imaging probe.

FIG. 1 is an illustration of an ultrasound system 10 including a transesophageal (TEE) imaging probe 300. The ultrasound imaging system 10 includes a TEE probe 12 including a probe handle 14 connected by a cable 16, a strain relief 17 and a connector 18 to an ultrasound control unit 20. The ultrasound control unit 20 generally includes, among other things, a processor 28, keyboard 22, beamformer 38, and display 24 connected via a logical interface 26. The beamformer 38 generally includes a transmit beamformer and a receive beamformer and is shown as a single element for simplicity. The processor 28 performs, among other processing tasks, image generation. The keyboard 22 is useful for inputting commands to the ultrasound control unit 20 and the display 24 is used to view ultrasonic images developed by the TEE probe 12 and the control unit 20.

The TEE probe 12 includes a distal end 30 connected to an elongated semi-flexible body 36. The proximal end of the semi-flexible body 36 is connected to the distal end 30 of the probe handle 14. The distal end 30 includes a rigid region 32 and a flexible region 34, which is connected to the distal end 30 of the semi-flexible body 36. The probe handle 14 includes a positioning control unit 15 for articulating the flexible region 34 and thus orienting the rigid region 32 relative to the tissue being imaged. The elongated semi-flexible body 36 is constructed and arranged for insertion into the esophagus.

Figure 2A:
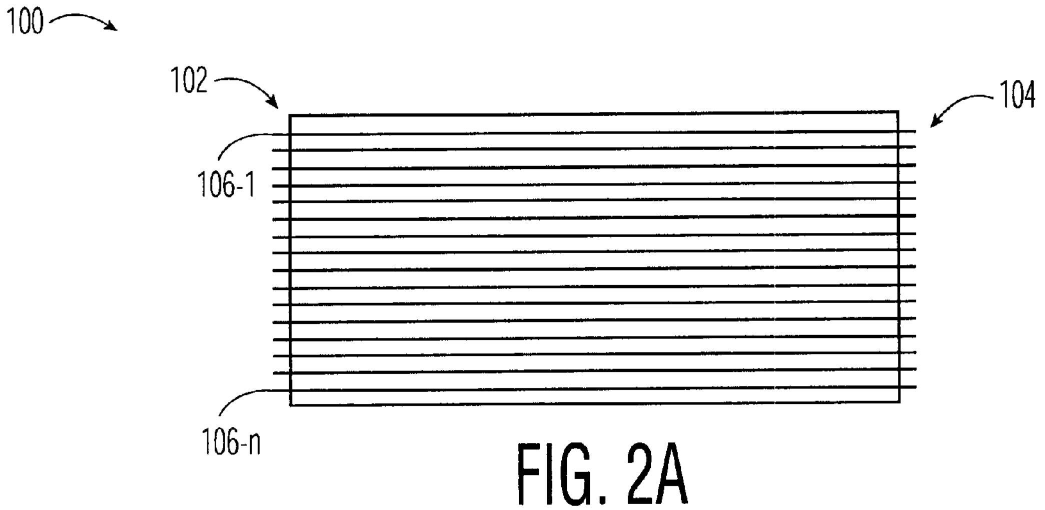
FIG. 2A is a plan view illustrating a ribbon cable that is connected inside the TEE probe of FIG. 1.

FIG. 2A is a plan view illustrating a ribbon cable 100 that is internally connected within the TEE probe 12 of FIG. 1. The ribbon cable 100 includes a first end 102 and a second end 104. The ribbon cable 100 includes a plurality of individual conductors 106-1 through 106-n, individually referred to as a conductor 106. The conductors 106 may be coaxial conductors, in which case each conductor 106 includes a center conductor, a dielectric, and a shield, enclosed within an outer insulator. Alternatively, the conductors 106 may be individual signal and return (ground) conductors that are fabricated into a ribbon cable. An example of such a ribbon cable is the FLAT OUT!™ flat ribbon cable available from W. L. Gore & Associates, Inc. of Phoenix, Ariz. A plurality of the individual conductors 106 are bonded together to form a ribbon cable using techniques that are known to those having ordinary skill in the art.

Figure 2B:
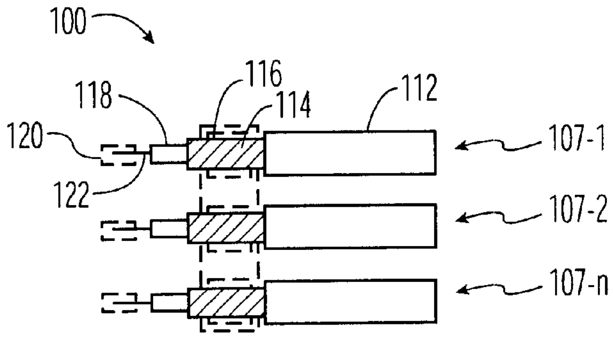
FIG. 2B is a detailed schematic view illustrating the conductor of FIG. 2A when implemented using coaxial conductors.

FIG. 2B is a detailed schematic view illustrating the conductor 106 of FIG. 2A when implemented using coaxial conductors 107. The conductors 107-1 through 107-n, as shown in FIG. 2B, is a coaxial conductor including an outer jacket 112, a braided or otherwise interlaced ground shield 114, which may include a metallic under wrap, dielectric material 118, and a center conductor 122. As illustrated in FIG. 2B, the center conductor 122 is coupled to the circuit land 120 using, for example, but not limited to, ultrasonic wire bonding (also known as thermosonic wire bonding), tab bonding, soldering or other methods of attachment. Similarly, the ground shield 114 is electrically coupled to a solder land 116. While each center conductor 122 of each coaxial cable 107 is coupled to an individual circuit land 120, the ground shield 114 can be connected to a common land 116. In other words, the common land 116 will connect all the ground shield conductors of each coaxial conductor 107-1 through 107-n.

Figure 2C:
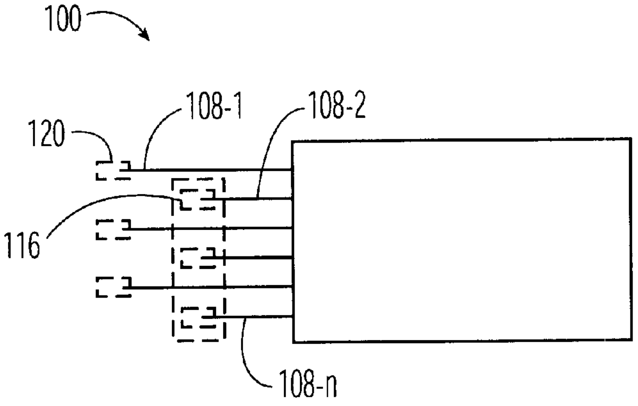
FIG. 2C is a schematic view illustrating an alternative implementation of the ribbon cable of FIG. 2A.

FIG. 2C is a schematic view illustrating an alternative implementation of the ribbon cable 100 of FIG. 2A The ribbon cable 100 includes a plurality of conductors 108-1 through 108-n arranged in an alternating pattern to include a signal conductor, for example 108-1, followed by a return conductor 108-2 and so on. Each conductor 108-1 and 108-2 is electrically coupled to a corresponding solder land 120 and 116, respectively, as shown in FIG. 2C. If arranged in an alternating manner, the signal conductor 108-1 and the return conductor 108-2 continue in this alternating pattern so that the solder land 116 can be, for example, a continuous ground bus. Alternatively, the ribbon cable 100 can include only signal or return conductors and a plurality of the ribbon cables can be vertically stacked (to be described with reference to FIG. 3) to improve signal isolation. In such an arrangement, all the conductors in the non-signal ribbon cable can be bussed together at one or both ends. The ribbon cable 100 can be, for example, the FLAT OUT!™ ribbon cable available from W. L. Gore & Associates, Inc. of Phoenix, Ariz.

Figure 3:
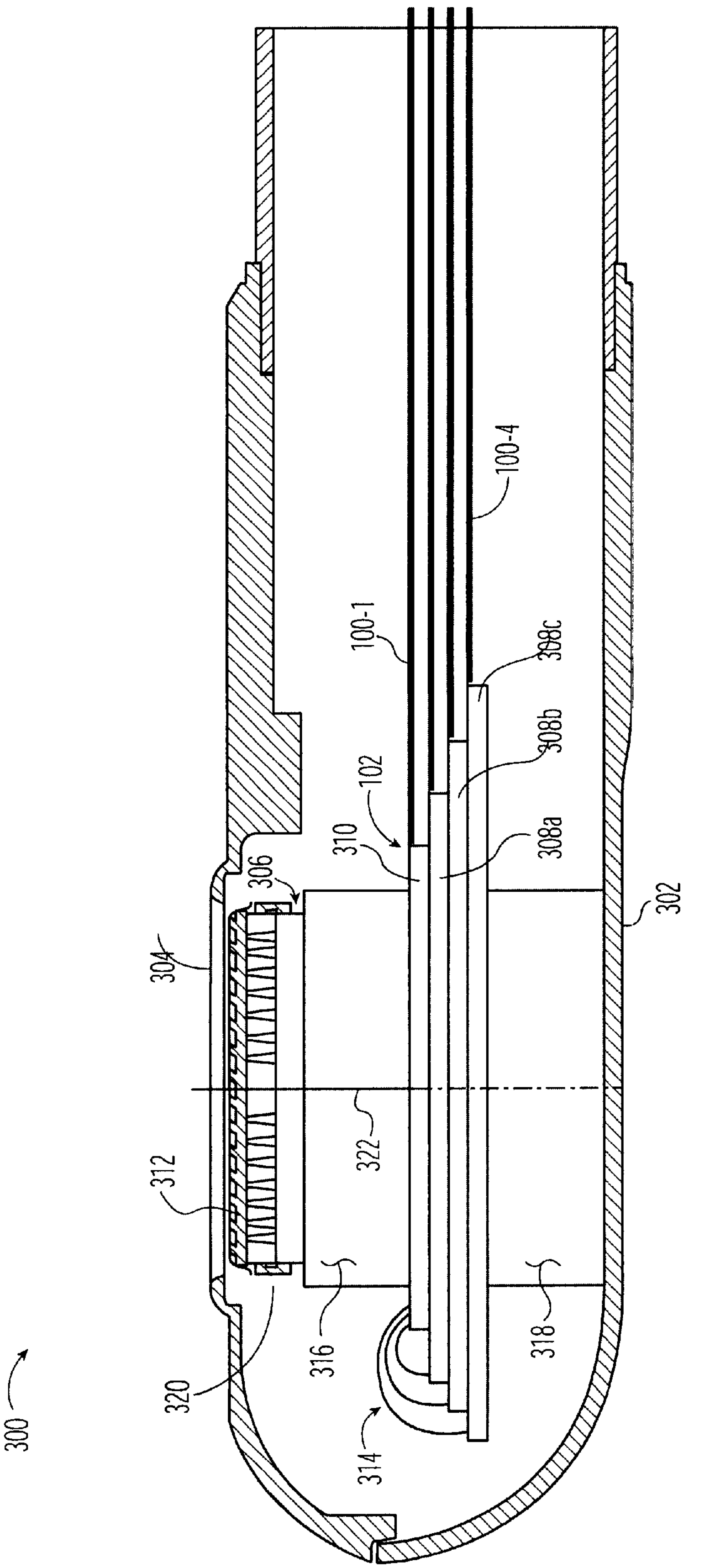
FIG. 3 is a cross-sectional view of a TEE probe constructed in accordance with an aspect of the invention.

FIG. 3 is a cross-sectional view of a TEE probe 300 constructed in accordance with an aspect of the invention. The TEE probe 300 uses one or more ribbon cables, four of which are illustrated using reference numerals 100-1 through 100-4, to provide electrical connection within the TEE probe 300. The TEE probe 300 includes a housing 302 that includes an acoustic window 304 through which ultrasonic imaging is performed. The housing 302 includes a transducer assembly 306 located behind the acoustic window 304. The transducer assembly 306 includes a matrix of transducer elements 312. As with prior transesophageal imaging probes, the TEE probe 300 is connected to an elongated semiflexible body (as shown in FIG. 1). The elongated semi-flexible body is, in turn, connected to a probe handle (FIG. 1).

The transducer assembly 306 includes a plurality of circuit boards, exemplar ones of which are illustrated using reference numerals 308*a,* 308*b* and 308*c.* Although shown using three circuit boards, the invention is applicable to a transducer assembly 306 that includes fewer or more circuit boards. Each circuit board 308*a,* 308*b* and 308*c,* includes a first and second set of lands to which electrical connections may be made. The lands on the circuit boards are typically regions that are suitable for electrical connection. The circuit board 308*a* is fixed to an integrated circuit (IC) 310. The IC 310 also includes a first and second set of lands. The IC 310 distributes the signals carried by the ribbon cables 100-1 through 1004 to the matrix of transducer elements 312. Due to space limitations dictated by the pitch of connections to the IC 310 and the number of required connections, the lands are spread over two edges of the IC 310. In accordance with an aspect of the invention, the circuit boards 308*a,* 308*b* and 308*c* act as pass-through connections, thereby interfacing a portion of the conductors of the ribbon cables 100-1 through 1004 with the lands on the IC 310. The first end 102 of the ribbon cable 100-1 is connected to a first set of lands on the IC 310 on a first edge of the IC 310, using, for example, but not limited to, ultrasonic wire bonding (also known as thermosonic wire bonding), tab bonding, etc. Furthermore, a first end 102 of the second ribbon cable 100-2 is connected to a first set of lands on a first end of the circuit board 308*a,* using, for example, ultrasonic wire bonding. The connections between the third ribbon cable 100-3 and the fourth ribbon cable 1004 to the second circuit board 308*b* and the third circuit board 308*c,* respectively, are done in similar fashion.

The circuit boards 308*a,* 308*b* and 308*c* provide a set of traces (not shown), that connect the first set of lands on each edge of each circuit board to a second set of lands on a second edge of each circuit board. The second set of lands on each circuit board 308*a,* 308*b* and 308*c* are connected to a second set of lands on a second edge of the IC 310. The IC 310 is preferably acoustically matched to each circuit board 308*a,* 308*b* and 308*c,* with each circuit board bonded together using a thin epoxy bond. The use of the circuit boards 308*a,* 308*b* and 308*c* provides a transducer assembly with improved thermoconductivity and better acoustic properties than simply running each ribbon cable 100 directly to the second set of lands on the IC 310.

As shown in FIG. 3, each successive circuit board 308*a,* 308*b* and 308*c* extends past the IC 310 and each previous circuit board on at least one edge of the IC 310, and as shown in FIG. 3, past at least two edges of the IC 310. Such an arrangement provides two different input surfaces separated both vertically and laterally. Preferably, the circuit boards 308*a*, 308*b* and 308*c* and the IC 310 are related to each other so as to provide access for the cables 100 to two sets of lands. The first set of lands being on a first edge of the IC 310, and a second set of lands being on the first edge of each circuit board 308. Preferably, each circuit board 308*a*, 308*b* and 308*c* has a lateral area (lateral being the direction along the extent of the probe 300) greater than the IC 310. However, those having ordinary skill in the art will understand that this need not be the case. For example, the IC 310 and each circuit board 308 could have the same lateral area (including a staggered relationship) or the IC 310 could have the greater lateral area.

As noted, the IC 310 is provided with at least two sets of lands, preferably on at least two edges thereof, and more preferably at opposite ends thereof The first set of lands has a pitch equivalent to the pitch of the conductors 106-1 through 106-n of each ribbon cable 100 and is positioned within the probe 300 to facilitate connections between the ribbon cable 100-1 and the IC 310. Similarly, each circuit board 308 is provided with at least two sets of lands, preferably on at least two edges thereof and more preferably on opposite ends thereof. The first set of lands on each circuit board 308 has a pitch equivalent to the pitch of the conductors 106-1 through 106-n of each subsequent ribbon cable 100-2 through 1004. The pitch of the second set of lands on the IC 310 and on the second set of lands on each circuit board 308 is dictated by the technology used to form the connections. For example, the IC 310 and each circuit board 308 may be electrically connected by a plurality of wires 314 extending between the second set of lands on the IC 310 and the second set of lands on each circuit board 308*a*, 308*b* and 308*c*. Preferably, ultrasonic wire bonding is also used to connect the wires 314 to the lands on the IC 310 and to the lands on each circuit board 308.

The circuit boards 308*a*, 308*b* and 308*c* and the IC 310 are part of a transducer assembly 306, which can be thought of as a stack of layers. A first block 316, preferably made of heat dissipating material, may be situated above the IC 310, while a second block 318, also preferably made of heat dissipating material, may be situated below the lowest circuit board, in the example, 308*c*. The material forming the blocks 316 and 318 is also selected based on desired acoustic properties, as is known to those having ordinary skill in the art. For example, it is often desirable to absorb vibrations, which would leave one having ordinary skill in the art to form the blocks 316 and 318 out of acoustically absorptive material.

The connection between the IC 310 and the matrix of transducer elements 312 is beyond the scope of the invention. However, details of such connections can be found in co-pending commonly assigned U.S. patent application, assigned Ser. No. 09/919,470, entitled SYSTEM FOR ATTACHING AN ACOUSTIC ELEMENT TO AN INTEGRATED CIRCUIT. An alternative methodology for such a connection can be found in U.S. Pat. No. 5,267,221. Accordingly, only a brief explanation is provided.

A support system 320 provides support and some acoustic isolation for the matrix of transducer elements 312, and as such typically comprises at least a layer of backing material. A connection 322 provides electrical connectivity from the IC 310 to the matrix of transducer elements 312. The physical structure of the connection 322, and in particular the structure of the interface between the connection 322 and the matrix of transducer elements 312, may be any of a variety of known structures for connecting an IC to a matrix of transducer elements. The above-mentioned commonly assigned co-pending U.S. patent application Ser. No. 09/919,470, entitled SYSTEM FOR ATTACHING AN ACOUSTIC ELEMENT TO AN INTEGRATED CIRCUIT, describes several methods and apparatus for forming such a connection, including the use of a redistribution layer to match the pitch of the contacts on the IC 310 to the pitch of the matrix of transducer elements 312.

The structure shown in FIG. 3 permits the connection of a large number of leads to the matrix of transducer elements 312 in a relatively constrained area by using the circuit boards 308*a*, 308*b* and 308*c* to provide, in effect, additional sets of lands in close proximity to the first set of lands on the IC 310. An additional benefit of the configuration described in FIG. 3 is modularization, providing for more efficient assembly of the TEE probe 300. The illustrated configuration also promotes efficient heat dissipation and sound absorption without unwanted acoustic reflections (i.e., impedance matching).

Figure 4:
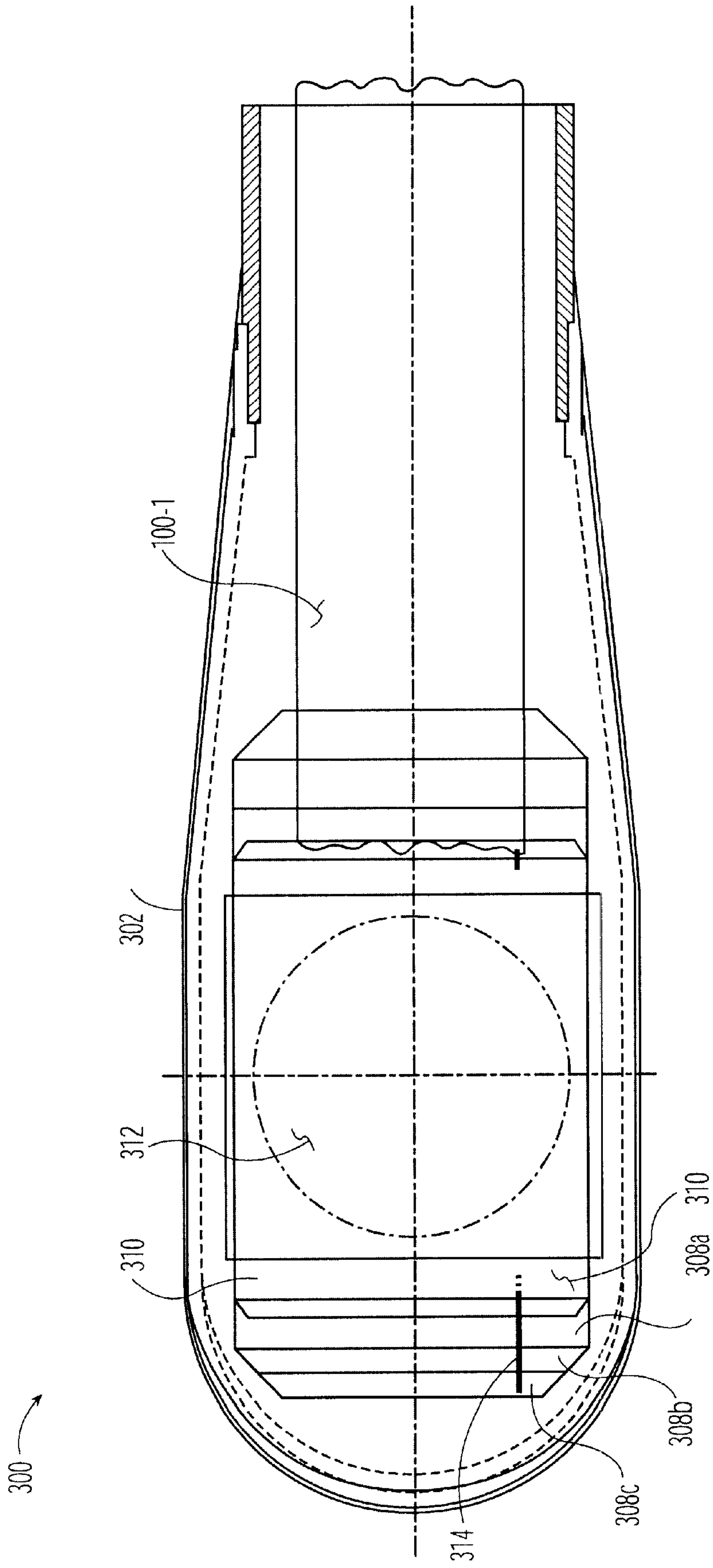
FIG. 4 is a plan view illustrating the TEE probe of FIG. 3.

FIG. 4 is a plan view illustrating the TEE probe 300 of FIG. 3. As shown in FIG. 4, the uppermost ribbon cable 100-1 connects to the first set of lands on the IC 310. The circuit boards 308*a*, 308*b* and 308*c* are located below the IC 310. Each circuit board 308 includes a second set of lands that are connected via wires 314 to a second set of lands on the IC 310.

Figure 5:
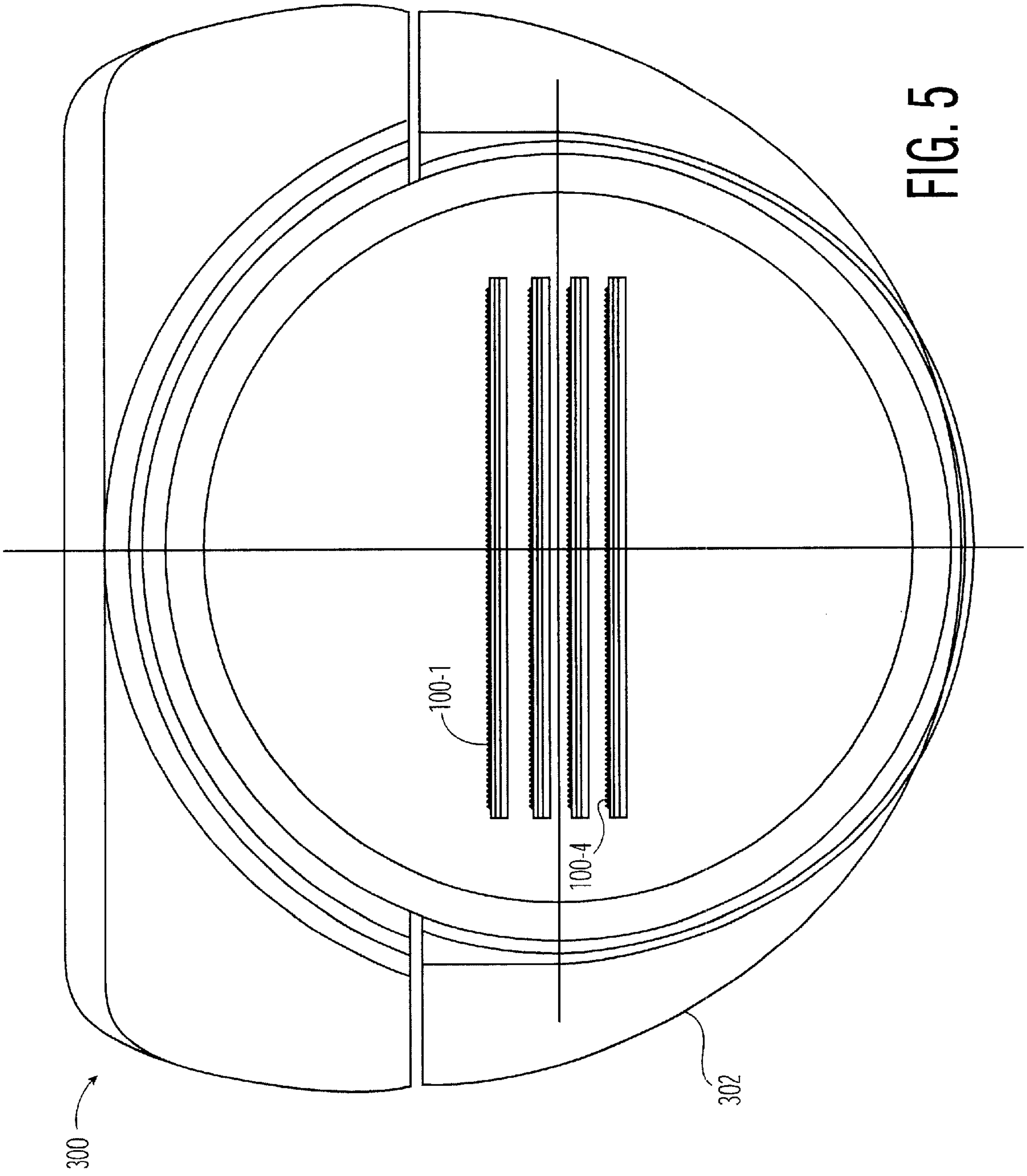
FIG. 5 is a cross-sectional end view of the TEE probe of FIGS. 3 and 4.

FIG. 5 is a cross-sectional end view of the TEE probe 300 of FIGS. 3 and 4. As shown in FIG. 5, the four ribbon cables 100-1 through 1004 are stacked vertically within the probe housing 302.

Figure 6:
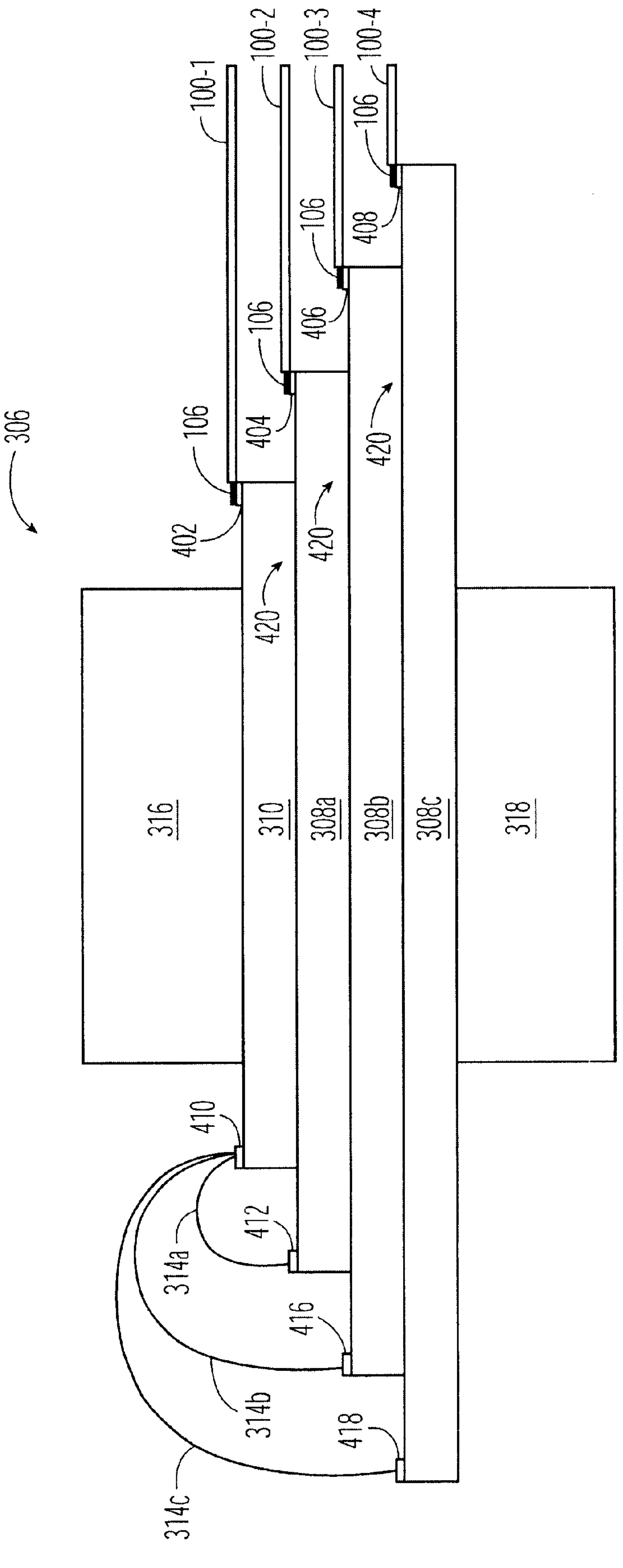
FIG. 6 is a cross-sectional view illustrating the connections between the ribbon cables and portions of the transducer assembly of FIG. 3.

FIG. 6 is a cross-sectional view illustrating the connections between the ribbon cables 100 and portions of the transducer assembly 306 of FIG. 3. The circuit boards 308*a*, 308*b* and 308*c* are supported by block 318 and are joined together using, for example, a thin epoxy bond 420. The circuit board 308*a* is also joined to the IC 310 using a similar thin epoxy bond 420. The IC 310 includes a first set of lands 402 and a second set of lands 410. As shown in FIG. 6, the first set of lands 402 is located on an opposite side of the IC 310 from the second set of lands 410. Each of the circuit boards 308*a*, 308*b* and 308*c* also includes a first set of lands 404, 406, 408, respectively, and a second set of lands 412, 416 and 418, respectively. Each ribbon cable 100 is coupled to the IC 310 or a respective circuit board 308. For example, the conductors 106 of ribbon cable 100-1 are ultrasonically wire bonded to respective first lands 402 on the IC 310. Similarly, the conductors 106 of ribbon cables 100-2, 100-3 and 100-4 are similarly respectively bonded to the first set of lands 404, 406 and 408 on each of the circuit boards 308*a*, 308*b* and 308*c*. If the ribbon cables 100 contain a ground plane, the ground plane can be connected to the IC 310 using a variety of techniques, including, but not limited to, the use of an additional wire or by dedicating a wire within the ribbon cable 100 to the ground plane.

In accordance with an aspect of the invention, a second set of lands 412, 416 and 418 associated with each of the circuit boards 308*a*, 308*b* and 308*c*, respectively, are staggered as shown and used to transfer signals from ribbon cables 100-2, 100-3 and 100-4 to a corresponding second set of lands on the IC 310. This is accomplished using a plurality of wires 314*a*, 314*b* and 314*c*. The wires 314*a*, 314*b* and 314*c* can be bonded to the lands 410, 412, 416 and 418 using, for example, but not limited to ultrasonic wire bonding, thermosonic bonding or a ball bond. In this manner, the space restraint dictated by the shape of the TEE probe 300 can be alleviated through the use of such a signal distribution system as shown in FIG. 6.

It will be apparent to those skilled in the art that many modifications and variations may be made to the exemplar embodiments of the present invention set forth above, without departing substantially from the principles of the present invention. For example, the present invention can be used with piezoelectric ceramic and MUT transducer elements. Furthermore, the invention is applicable to different types of wiring applications and different types of transducer probes. All such modifications and variations are intended to be included herein.

What is claimed is:

1. A method for wiring an ultrasonic transducer, the method comprising:

electrically coupling a first ribbon cable to first lands on an integrated circuit (IC);

electrically coupling a second ribbon cable to first lands on a circuit board; and electrically coupling second lands on the circuit board to second lands on the integrated circuit.

2. The method of claim 1, further comprising bonding the circuit board to a surface of the IC.

3. The method of claim 1, further comprising coupling the IC to a matrix of transducer elements.

4. The method of claim 1, wherein the circuit board extends past the IC in at least one dimension.

5. The method of claim 1, wherein the first ribbon cable and the second ribbon cable are stacked vertically.

6. The method of claim 1, wherein the ultrasonic transducer is a transesophageal (TEE) probe.

7. The method of claim 1, wherein the first ribbon cable and the second ribbon cable include coaxial conductors.

8. The method of claim 1, wherein the first ribbon cable and the second ribbon cable include individual signal and ground conductors.

9. An ultrasonic transducer probe, comprising:

a transducer assembly including a matrix of transducer elements electrically coupled to an integrated circuit (IC), the IC including a first set of lands and a second set of lands;

a circuit board associated with the IC, the circuit board including a first set of lands and a second set of lands;

a first ribbon cable coupled to the first set of lands on the IC;

a second ribbon cable coupled to the first set of lands on the circuit board; and means for coupling the second set of lands on the IC to the second set of lands on the circuit board.

10. The transducer probe of claim 9, wherein the circuit board is bonded to a surface of the IC.

11. The transducer probe of claim 9, wherein the circuit board extends past the IC in at least one dimension.

12. The transducer probe of claim 9, wherein the first ribbon cable and the second ribbon cable are stacked vertically.

13. The transducer probe of claim 9, wherein the ultrasonic transducer probe is a transesophageal (TEE) probe.

14. The transducer probe of claim 9, wherein the first ribbon cable and the second ribbon cable include coaxial conductors.

15. The transducer probe of claim 9, wherein the first ribbon cable and the second ribbon cable include individual signal and ground conductors.

16. The transducer probe of claim 9, wherein the coupling means is a plurality of wires that are bonded to the second set of lands on the IC and the second set of lands on the circuit board.

17. A ultrasonic transesophageal (TEE) transducer probe, comprising:

a TEE transducer probe including a transducer assembly, the transducer assembly including a matrix of transducer elements electrically coupled to an integrated circuit (IC), the IC including a first set of lands and a second set of lands;

a circuit board associated with the IC, the circuit board including a first set of lands and a second set of lands;

a first ribbon cable coupled to the first set of lands on the IC;

a second ribbon cable coupled to the first set of lands on the circuit board; and means for coupling the second set of lands on the IC to the second set of lands on the circuit board.

18. The transducer probe of claim 17, wherein the circuit board is bonded to a surface of the IC.

19. The transducer probe of claim 17, wherein the circuit board extends past the IC in at least one dimension.

20. The transducer probe of claim 17, wherein the first ribbon cable and the second ribbon cable are stacked vertically.

21. The transducer probe of claim 17, wherein the first ribbon cable and the second ribbon cable include coaxial conductors.

22. The transducer probe of claim 17, wherein the first ribbon cable and the second ribbon cable include individual signal and ground conductors.

23. The transducer probe of claim 17, wherein the coupling means is a plurality of wires that are bonded to the second set of lands on the IC and the second set of lands on the circuit board.

* * * * *